US006384059B1

(12) United States Patent
Lövqvist et al.

(10) Patent No.: US 6,384,059 B1
(45) Date of Patent: *May 7, 2002

(54) CRYSTALLINE FORM OF OMEPRAZOLE

(75) Inventors: Karin Lövqvist, Mölndal; Gunnel Sundén, Göteborg; David Noreland, Södertälje; Ingvar Ymén, Saltsjö-Boo, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/640,097

(22) Filed: Aug. 15, 2000

Related U.S. Application Data

(63) Continuation of application No. 09/202,251, filed as application No. PCT/SE98/02028 on Nov. 10, 1998, now Pat. No. 6,150,380.

(51) Int. Cl.[7] .................. A61K 31/4439; C07D 401/12
(52) U.S. Cl. ..................................... 514/338; 546/273.7
(58) Field of Search ........................ 514/338; 546/273.7

(56) References Cited

U.S. PATENT DOCUMENTS

| | | | |
|---|---|---|---|
| 4,337,257 A | 6/1982 | Junggren et al. | 514/338 |
| 4,738,974 A | 4/1988 | Brändström | 514/338 |
| 5,314,506 A | 5/1994 | Midler et al. | 23/295 |
| 5,690,960 A | 11/1997 | Bengtsson et al. | 514/338 |
| 5,714,505 A | 2/1998 | Hasselkus | 514/338 |
| 5,856,493 A | 1/1999 | Ward et al. | 546/197 |
| 5,877,192 A | 3/1999 | Lindberg et al. | 514/338 |
| 5,900,424 A | 5/1999 | Källstrom et al. | 514/338 |

FOREIGN PATENT DOCUMENTS

| | | |
|---|---|---|
| EP | 5129 | 4/1981 |
| JP | 533752 | 6/1992 |
| WO | 9722603 | 6/1997 |
| WO | 9821201 | 5/1998 |
| WO | 9925711 | 5/1999 |

OTHER PUBLICATIONS

Cairns et al., Journal of Chromatography,. "Enantioselective high performance liquid chromatographic determination of omeprazole in human plasma", pp. 323–328 (1995).

Erlandsson et al., Journal of Chromatography, "Resolution of the enantiomers of omeprazole and some analogues by liquid chromatography on a trisphenylcarbamoylcellulose-based stationary phase; The effect of the enantiomers of omeprazole on gastric glands", pp. 305–319 (1990).

Ohishi et al., "Structure of 5–Methoxy–2–{[–methoxy–3, 5–dimethyl–2–pyridinyl)methyl] sulfiny}–1H–benzimidazole (Omeprazole)", pp. 1921–1323 (1989).

Heneck et al., "Polymorphie von Arzneistoffen", Pharm. Ind., 59, 1997, 165–169 CN 1160050.

Brändström, A. et al., "Structure activity relationships of substituted benzimidazoles", Scandinavian Journal of Gastroenterology, 20: Supplemental 108, 15–22 (1985).

*Primary Examiner*—Jane Fan
(74) *Attorney, Agent, or Firm*—White & Case LLP

(57) ABSTRACT

The present invention relates to a novel crystalline form of 5-methoxy-2-[[(4-methoxy-3,5-dimethyl-2-pyridinyl) methyl]sulfinyl-1H-benzimidazole, known under the generic name omeprazole. Further, the present invention also relates to the use of the novel crystalline form of 5-methoxy-2-[[(4-methoxy-3,5-dimethyl-2-pyridinyl) methyl]sulfinyl]-1H-benzimidazole for the treatment of gastrointestinal disorders, pharmaceutical compositions containing it as well as processes for the preparation of the novel crystalline form of 5-methoxy-2-[[(4-methoxy-3,5-dimethyl-2-pyridinyl)methyl]sulfinyl]-1H-benzimidazole.

12 Claims, 1 Drawing Sheet

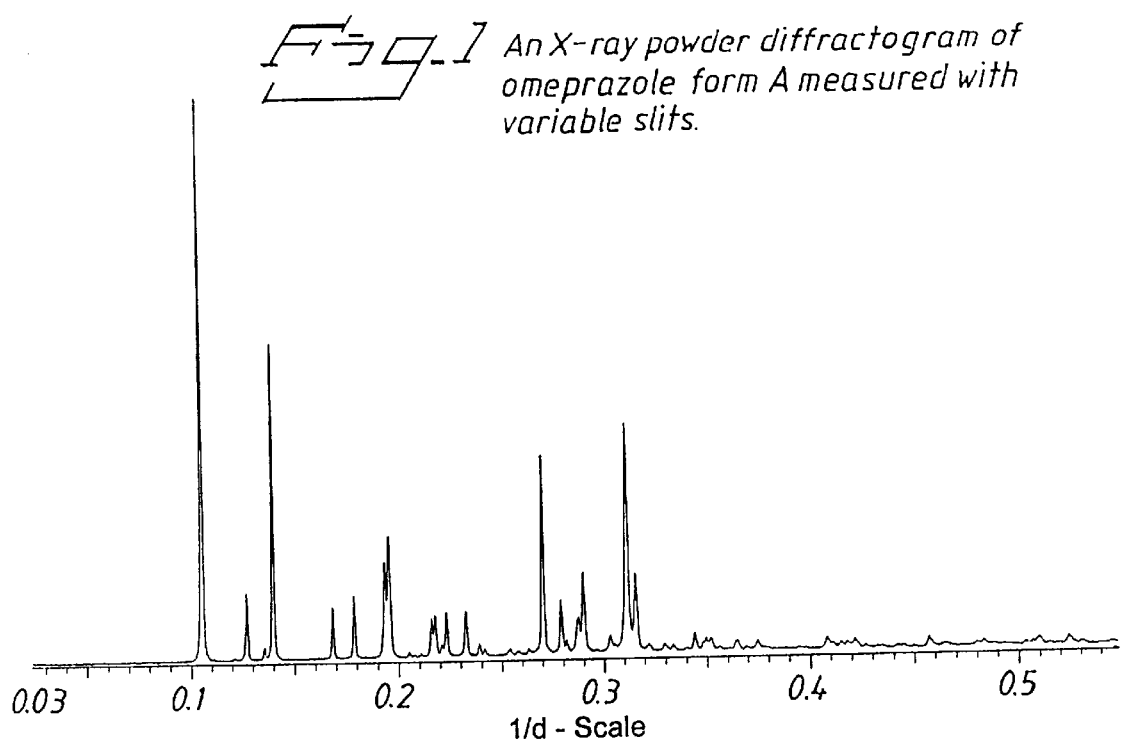
Fig. 1 An X-ray powder diffractogram of omeprazole form A measured with variable slits.
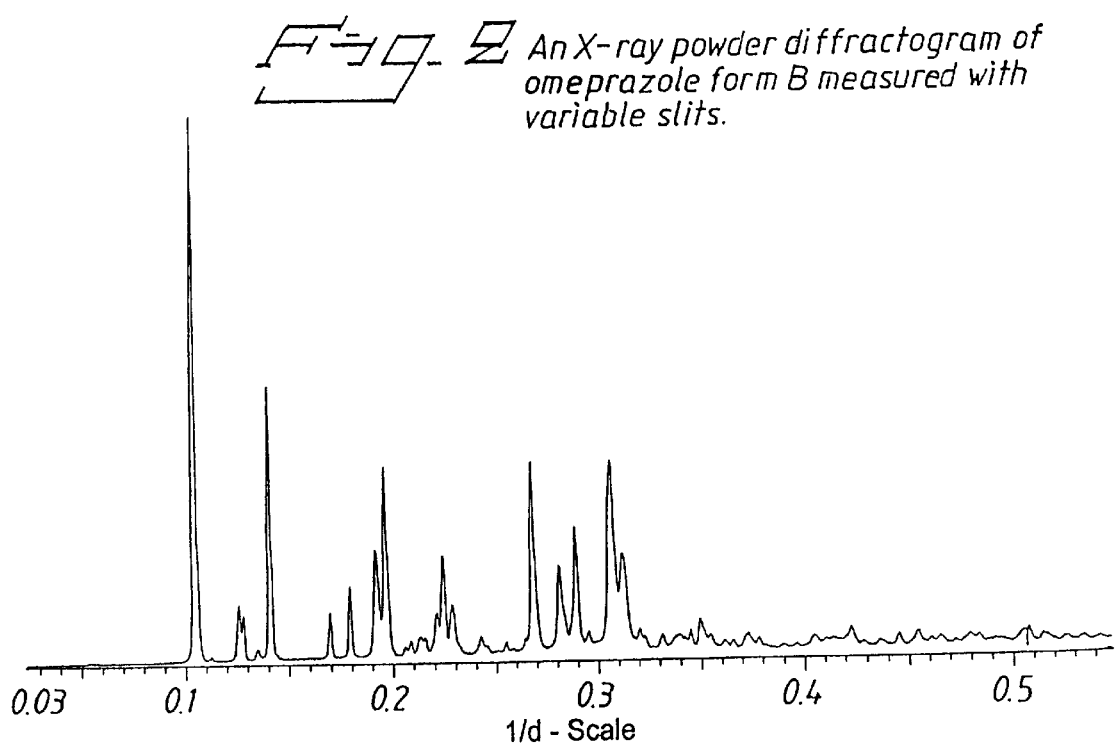
Fig. 2 An X-ray powder diffractogram of omeprazole form B measured with variable slits.

CRYSTALLINE FORM OF OMEPRAZOLE

This application is a continuation of application Ser. No. 09/202,251, filed on Dec. 10, 1998, now U.S. Pat. No. 6,150,380, which is a 371 of PCT/SE98/02028, filed Nov. 10, 1998.

FIELD OF THE INVENTION

The present invention relates to a novel crystalline form of 5-methoxy-2[[(4-methoxy-3,5-dimethyl-2-pyridinyl) methyl]sulfinyl]-1H-benzimidazole 5-methoxy-2-[[(4-methoxy-3,5-dimethyl-2-pyridinyl)methyl]sulfinyl]-1 H-benzimidazole is known under the generic name omeprazole and its novel crystalline form is hereinafter referred to as omeprazole form A. Further, the present invention also relates to use of omeprazole form A for the treatment of gastrointestinal disorders, pharmaceutical compositions containing omeprazole form A and processes for the preparation of omeprazole form A.

BACKGROUND OF THE INVENTION PRIOR ART

The compound 5-methoxy-2-[[(4-methoxy-3,5-dimethyl-2-pyridinyl)methyl]sulfinyl]-1H-benzimidazole, having the generic name omeprazole, as well as therapeutically acceptable salts thereof, are described in EP 5129. The single crystal X-ray data and the derived molecular structure of the so far only known crystal form of omeprazole is described by Ohishi et al., Acta Cryst. (1989), C45, 1921–1923. This published crystal form of omeprazole is hereinafter referred to as omeprazole form B.

Omeprazole is a proton pump inhibitor, i.e. effective in inhibiting gastric acid secretion, and is useful as an antiulcer agent. In a more general sense, omeprazole may be used for treatment of gastric-acid related diseases in mammals and especially in man.

BRIEF DESCRIPTION OF THE DRAWINGS

FIG. 1 is an X-ray powder diffractogram of omeprazole form A.

FIG. 2 is an X-ray powder diffractogram of omeprazole form B.

DESCRIPTION OF THE INVENTION

It has surprisingly been found that the substance omeprazole can exist in more than one crystal form. It is an object of the present invention to provide omeprazole form A. Another object of the present invention is to provide a process for the preparation of omeprazole form A, substantially free from other forms of omeprazole. X-ray powder diffraction (XRPD) is used as a method of differentiating omeprazole form A from other crystalline and non-crystalline forms of omeprazole. Additionally it is an object of the present invention to provide pharmaceutical formulations comprising omeprazole form A.

Omeprazole form A is a crystalline form exhibiting advantageous properties, such as being well-defined, being thermodynamically more stable and less hygroscopic than omeprazole form B, especially at room temperature. Omeprazole form A does also show a better chemical stability, such as thermo stability and light stability, than omeprazole form B.

Omeprazole form B can under certain conditions, completely or partly, be converted into omeprazole form A. Omeprazole form A is thereby characterized in being thermo-dynamically more stable than omeprazole form B.

Omeprazole form A is further characterized as being essentially non-hygroscopic.

Omeprazole form A is characterized by the positions and intensities of the peaks in the X-ray powder diffractogram, as well as by the unit cell parameters. The unit cell dimensions have been calculated from accurate Guinier data. The X-ray powder diffractogram data as well as the unit cell parameters for omeprazole form B are different compared to omeprazole form A. Omeprazole form A can thereby be distinguished from omeprazole form B, using X-ray powder diffraction.

Omeprazole form A, according to the present invention, is characterized in providing an X-ray powder diffraction pattern, as in FIG. 1, exhibiting substantially the following d-values and intensities;

| Form A | | Form A | |
|---|---|---|---|
| d-value (Å) | Relative intensity | d-value (Å) | Relative intensity |
| 9.5 | vs | 3.71 | s |
| 7.9 | s | 3.59 | m |
| 7.4 | w | 3.48 | m |
| 7.2 | vs | 3.45 | s |
| 6.0 | m | 3.31 | w |
| 5.6 | s | 3.22 | s |
| 5.2 | s | 3.17 | m |
| 5.1 | s | 3.11 | w |
| 4.89 | w | 3.04 | w |
| 4.64 | m | 3.00 | w |
| 4.60 | m | 2.91 | w |
| 4.53 | w | 2.86 | w |
| 4.49 | m | 2.85 | w |
| 4.31 | m | 2.75 | w |
| 4.19 | w | 2.67 | w |
| 4.15 | w | 2.45 | w |
| 3.95 | w | 2.41 | w |

The peaks, identified with d-values calculated from the Bragg formula and intensities, have been extracted from the Guinier diffractogram of omeprazole form A. The relative intensities are less reliable and instead of numerical values the following definitions are used;

| % Relative Intensity* | Definition |
|---|---|
| 25–100 | vs (very strong) |
| 10–25 | s (strong) |
| 3–10 | m (medium) |
| 1–3 | w (weak) |

*The relative intensities are derived from diffractograms measured with fixed slits.

Omeprazole form A according to the present invention is further characterized by a triclinic unit cell with parameters;

a=10.410(4)Å
b=10.468(3)Å
c=9.729(4)Å
α=111.51(3)°
β=116.78(3)°
γ=90.77(3)°

Omeprazole form A can also be characterized by Raman spectroscopy, where omeprazole form A is characterized by the absence of a band at 1364 cm$^{-1}$, which is observed for omeprazole form B, and by the ratio of the relative intensities of the 842 and 836 cm$^{-1}$ bands. The ratio (intensity of 842 cm-1 band/intensity of 836 cm-1 band) is<1 for omeprazole form A, while the ratio is>1 for omeprazole form B.

According to the invention there is further provided a process for the preparation of omeprazole form A.

Omeprazole form A is obtained upon slow crystallization and omeprazole form B is obtained from fast crystallization. Omeprazole form A may be prepared by reaction crystallisation or recrystallizing omeprazole of any form, or mixtures of any forms, in an appropriate solvent, such as for instance methanol, at around room temperature and for a prolonged time period. Examples of prolonged time periods include, but are not limited to, a few hours, such as 2 hours, up to several weeks. Suitable solvents are alkyl alcohols and especially a lower alcohol comprising 1–4 carbon atoms.

Omeprazole form A may also be prepared by suspending omeprazole of any form, or mixtures of any forms, in an appropriate solvent at around room temperature and for a prolonged time period. Examples of appropriate solvents include, but are not limited to, methanol, ethanol, acetone, ethyl acetate, methyl tert, butyl ether, toluene, or any mixture thereof. Examples of prolonged time periods include, but are not limited to, a few hours, such as 2 hours, up to several weeks.

The omeprazole form A obtained according to the present invention is substantially free from other crystal and non-crystal forms of omeprazole, such as omeprazole form B. Substantially free from other forms of omeprazole shall be understood to mean that omeprazole form A contains less than 10%, preferably less than 5%, of any other forms of omeprazole, e.g. omeprazole form B.

Omeprazole form A in mixture with other solid form/forms of omeprazole, e.g. omeprazole form B, also exhibits advantageous properties, such as being chemically more stable than pure omeprazole form B. Mixtures comprising a certain amount of omeprazole form A, by weight, are also chemically more stable than other mixtures comprising a lesser amount of omeprazole form A, by weight. Such mixtures comprising omeprazole form A can be prepared, for example, by mixing omeprazole form A prepared according to the present invention with other solid forms of omeprazole, such as form B, prepared according to prior art.

The present invention also relates to mixtures comprising omeprazole form A in mixture with other solid forms of omeprazole. Such mixtures comprising omeprazole form A include for instance mixtures containing a detectable amount of omeprazole form A, 1%, 2%, 5%, 10%, 20%, 30%, 40%, 50%, 60%, 70%, 80%, 90%, 95%, 98% or 99% weight), of omeprazole form A.

Examples of other solid forms of omeprazole include, but are not limited to, omeprazole form B, amorphous forms, and other polymorphs.

A detectable amount of omeprazole form A is an amount that can be detected using conventional techniques, such as FT-IR, Raman spectroscopy, XRPD and the like.

The expression chemical stability includes, but is not limited to, thermo stability and light stability.

The compound of the invention, i.e. omeprazole form A, prepared according to the present invention is analyzed, characterized and differentiated from omeprazole form B by X-ray powder diffraction, a technique which is known per se. Another suitable technique to analyze, characterize and differentiate omeprazole form A from omeprazole form B is by Raman spectroscopy:

Omeprazole form A is effective as a gastric acid secretion inhibitor, and is useful as an antiulcer agent. In a more general sense, it can be used for treatment of gastric-acid related conditions in mammals and especially in man, including e.g. reflux esophagitis, gastritis, duodenitis, gastric ulcer and duodenal ulcer. Furthermore, it may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. The compound of the invention may also be used in patients in intensive care situations, in patients with acute upper gastrointestinal bleeding, pre- and postoperatively to prevent aspiration of gastric acid and to treat stress ulceration. Further, the compound of the invention may be useful in the treatment of psoriasis as well as in the treatment of Helicobacter infections and diseases related to these. The compound of the invention may also be used for treatment of inflammatory conditions in mammals, including man.

Any suitable route of administration may be employed for providing the patient with an effective dosage of omeprazole form A according to the invention. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of omeprazole. In all dosage forms omeprazole form A can be admixtured with other suitable constituents.

According to the invention there is further provided a pharmaceutical composition comprising omeprazole form A, as active ingredient, in association with a pharmaceutically acceptable carrier, diluent or excipient and optionally other therapeutic ingredients. Compositions comprising other therapeutic ingredients are especially of interest in the treatment of Helicobacter infections. The invention also provides the use of omeprazole form A in the manufacture of a medicament for use in the treatment of a gastric-acid related condition and a method of treating a gastric-acid related condition which method comprises administering to a subject suffering from said condition a therapeutically effective amount of omeprazole form A.

The compositions of the invention include compositions suitable for peroral or parenteral administration. The compositions may be conveniently presented in unit dosage forms, and prepared by any methods known in the art of pharmacy.

In the practice of the invention, the most suitable route of administration as well as the magnitude of a therapeutic dose of omeprazole form A in any given case will depend on the nature and severity of the disease to be treated. The dose, and dose frequency, may also vary according to the age, body weight, and response of the individual patient. Special requirements may be needed for patients having Zollinger-Ellison syndrome, such as a need for higher doses than the average patient. Children and patients with liver diseases as well as patients under long term treatment will generally benefit from doses that are somewhat lower than the average. Thus, in some conditions it may be necessary to use doses outside the ranges stated below. Such higher and lower doses are within the scope of the present invention.

In general, a suitable oral dosage form may cover a dose range from 5 mg to 250 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 247 983, the disclosures of which are hereby incorporated as a whole by reference.

Combination therapies comprising omeprazole form A and other active ingredients in separate dosage forms, or in one fixed dosage form, may also be used. Examples of such active ingredients include anti-bacterial compounds, non-steroidal anti-inflammatory agents, antacid agents, alginates and prokinetic agents.

The examples which follow will further illustrate the preparation of the compound of the invention, i.e. omeprazole form A, but are not intended to limit the scope of the invention as defined hereinabove or as claimed below.

EXAMPLES

Example 1

Preparation of Omeprazole form A

Omeprazole (55.8 g) is added at room temperature to methanol (348 ml) containing ammonia (1.3 ml; 25%). The suspension is thereafter stirred in darkness for approximately 45 hours and then filtered. The filtrate is dried 18 hours at 30° C. under reduced pressure (<5 mbar). Yield: 43.9 g.

Example 2

Preparation of Omeprazole Form B

Omeprazole (50 g) is added to methanol (750 ml) containing ammonia (0.7 ml; 25%) at 50° C. The solution is thereafter filtered and cooled in about 20 minutes to approximately 0C. The formed crystals are filtered and washed with ice cooled methanol and then dried. The filtrate was dried 24 hours at 40° C. under reduced pressure (<5 mbar). Yield: 39 g.

Example 3

Characterization of Omeprazole Form A and Omeprazole Form B using X-ray Powder Diffraction X-ray diffraction analysis was performed according to standard methods which can be found in e.g. Bunn, C. W. (1948), Chemical Crystallography, Clarendon Press, London; or Klug, H. P. & Alexander, L. E. (1974), X-Ray Diffraction Procedures, John Wiley and Sons, New York. The unit cell parameters for omeprazole form A and B have been calculated from the Guinier X-ray powder diffractograms using the program "TREOR" by Werner, P.-E., Eriksson,L. and Westdahl,M., J. Appl. Crystallogr. 18 (1985) 367–370. The fact that the positions of all peaks in the diffractograms for omeprazole form A and form B may be calculated using the respective unit cell parameters, proves that the unit cells are correct and that the diffractograms are indicative of the pure forms. The diffractogram of omeprazole form A, prepared according to Example 1 in the present application, is shown in FIG. 1 and the diffractogram of omeprazole form B, prepared according to Example 2 in the present application is shown in FIG. 2.

The peaks, identified with d-values calculated from the Bragg formula and intensities, have been extracted from the diffractograms for omeprazole forms A and form B, and are given in Table 1. In this table the unit cell parameters for omeprazole forms A and B are also given. The relative intensities are less reliable and instead of numerical values the following definitions are used;

| % Relative Intensity | Definition |
|---|---|
| 25–100 | vs (very strong) |
| 10–25 | s (strong) |
| 3–10 | m (medium) |
| 1–3 | w (weak) |

Some additional weak or very weak peaks found in the diffractograms have been omitted from table 1.

Table 1. X-ray powder diffraction data for omeprazole form A and form B shown in FIGS. 1 and 2. All peaks noted for omeprazole form A and form B can be indexed with the unit cells given below.

| Form A | | Form B | |
|---|---|---|---|
| d-value (Å) | Relative intensity | d-value (Å) | Relative intensity |
| 9.5 | vs | 9.6 | vs |
| 7.9 | s | 8.0 | m |
| 7.4 | w | 7.9 | m |
| 7.2 | vs | 7.5 | w |
| 6.0 | m | 7.1 | vs |
| 5.6 | s | 5.9 | m |
| 5.2 | s | 5.6 | m |
| 5.1 | s | 5.3 | s |
| 4.89 | w | 5.1 | s |
| 4.64 | m | 4.54 | m |
| 4.60 | m | 4.48 | s |
| 4.53 | w | 4.41 | m |
| 4.49 | m | 4.14 | w |
| 4.31 | m | 3.75 | s |
| 4.19 | w | 3.57 | m |
| 4.15 | w | 3.47 | s |
| 3.95 | w | 3.40 | w |
| 3.71 | s | 3.28 | s |
| 3.59 | m | 3.22 | m |
| 3.48 | m | 3.02 | w |
| 3.45 | s | 2.97 | w |
| 3.31 | w | 2.87 | w |
| 3.22 | s | 2.37 | w |
| 3.17 | m | | |
| 3.11 | w | | |
| 3.04 | w | | |
| 3.00 | w | | |
| 2.91 | w | | |
| 2.86 | w | | |
| 2.85 | w | | |
| 2.75 | w | | |
| 2.67 | w | | |
| 2.45 | w | | |
| 2.41 | w | | |

The triclinic unit cells are:

| Unit cell form A | Unit cell form B |
|---|---|
| a = 10.410(4) Å | a = 10.257(10) Å |
| b = 10.468(3) Å | b = 10.717(6) Å |
| c = 9.729(4) Å | c = 9.694(10) Å |
| α = 111.51(3)° | α = 112.14(7)° |
| β = 116.78(3)° | β = 115.56(5)° |
| γ = 90.77(3)° | γ = 91.76(7)° |

What is claimed is:
1. Omeprazole form A having a content within the range 90% to 99% by weight of an omeprazole substance providing an X-ray powder diffraction exhibiting substantially the following d-values:

| d-value (Å) | Relative intensity | d-value (Å) | Relative intensity |
|---|---|---|---|
| 9.5 | vs | 3.71 | s |
| 7.9 | s | 3.59 | m |
| 7.4 | w | 3.48 | m |
| 7.2 | vs | 3.45 | s |
| 6.0 | m | 3.31 | w |
| 5.6 | s | 3.22 | s |
| 5.2 | s | 3.17 | m |
| 5.1 | s | 3.11 | w |
| 4.89 | w | 3.04 | w |
| 4.64 | m | 3.00 | w |
| 4.60 | m | 2.91 | w |
| 4.53 | w | 2.86 | w |
| 4.49 | m | 2.85 | w |
| 4.31 | m | 2.75 | w |
| 4.19 | w | 2.67 | w |
| 4.15 | w | 2.45 | w |
| 3.95 | w | 2.41 | w |

2. Omeprazole form A according to claim 1, wherein the omeprazole substance is defined by a triclinic unit cell with parameters a=10.410(4) Å, b=10.468(3) Å, c=9.729(4) Å, α=111.51(3)°, β=116.78(3)°, γ=90.773(3)°.

3. Omeprazole form A according to claim 1, wherein the omeprazole substance is thermodynamically stable at room temperature.

4. Omeprazole form A according to claim 1, wherein the omeprazole substance is essentially non-hygroscopic.

5. Omeprazole form A according to claim 1, wherein 95% by weight of the omeprazole substance is present.

6. Omeprazole form A according to claim 1, wherein 98% by weight of the omeprazole substance is present.

7. Omeprazole form A according to claim 1, wherein 99% by weight of the omeprazole substance is present.

8. Omeprazole form A having a content within the range 90% to 99% by weight of an omeprazole substance, wherein, in a Raman spectroscopy, the omeprazole substance is identified by the absence of a band at 1364 $cm^{-1}$ and by the ratio of the relative intensities 842 $cm^{-1}$ band/ 836 $cm^{-1}$ band of <1.

9. A pharmaceutical formulation comprising a therapeutically effective amount of omeprazole form A according to claim 1 in admixture with a pharmaceutically acceptable excipient.

10. A method for inhibiting gastric acid secretion which comprises administration of a therapeutically effective amount of omeprazole form A according to claim 1 to a patient in need thereof.

11. A method for treating gastrointestinal inflammatory diseases which comprises administration of a therapeutically effective amount of omeprazole form A according to claim 1 to a patient in need thereof.

12. A method for the treatment of Helicobacter infections and diseases which comprises administration of a therapeutically effective amount of omeprazole form A according to claim 1 to a patient in need thereof.

* * * * *

UNITED STATES PATENT AND TRADEMARK OFFICE
CERTIFICATE OF CORRECTION

PATENT NO.    : 6,384,059 B1                                                Page 1 of 1
DATED         : May 7, 2002
INVENTOR(S)   : Lövqvist et al.

It is certified that error appears in the above-identified patent and that said Letters Patent is hereby corrected as shown below:

<u>Title page,</u>
Item [73], Assignee should be -- AstraZeneca AB --.

Signed and Sealed this

Fifteenth Day of October, 2002

Attest:

Attesting Officer

JAMES E. ROGAN
*Director of the United States Patent and Trademark Office*